(12) United States Patent
Margraf et al.

(10) Patent No.: US 10,406,271 B2
(45) Date of Patent: Sep. 10, 2019

(54) METHOD FOR FILTERING BLOOD TO PRODUCE PLASMA OR SERUM

(71) Applicant: LEUKOCARE AG, Munich (DE)

(72) Inventors: Stefan Margraf, Frankfurt am Main (DE); Martin Scholz, Oberursel (DE)

(73) Assignee: Leukocare AG (DE)

( * ) Notice: Subject to any disclaimer, the term of this patent is extended or adjusted under 35 U.S.C. 154(b) by 143 days.

(21) Appl. No.: 14/964,049

(22) Filed: Dec. 9, 2015

(65) Prior Publication Data

US 2016/0082174 A1 Mar. 24, 2016

Related U.S. Application Data

(62) Division of application No. 13/378,991, filed as application No. PCT/EP2010/058551 on Jun. 17, 2010.

(30) Foreign Application Priority Data

Jun. 17, 2009 (EP) .................................. 09163006

(51) Int. Cl.
*B01D 61/00* (2006.01)
*A61M 1/34* (2006.01)
(Continued)

(52) U.S. Cl.
CPC ............ *A61M 1/34* (2013.01); *A61M 1/3403* (2014.02); *B01D 63/087* (2013.01);
(Continued)

(58) Field of Classification Search
USPC ... 210/321.6, 321.8, 321.88, 321.89, 321.85, 210/416.1, 433.1, 497.01, 500.23, 210/503–506, 637, 645, 650, 651, 767, 210/741, 808; 422/99, 101, 102; 435/2, 435/7.1, 287.2; 436/170, 177, 178; 600/576, 577, 583
See application file for complete search history.

(56) References Cited

U.S. PATENT DOCUMENTS 3,705,100 A 12/1972 Blatt et al.
4,361,155 A 11/1982 Anastasio
(Continued)

FOREIGN PATENT DOCUMENTS

CN 1714292 A 12/2005
EP 0733378 A 9/1996
(Continued)

OTHER PUBLICATIONS

Steinmetz, Johannes, International Search Report and Written Opinion, PCT/EP2010/058551, European Patent Office, dated Nov. 24, 2010.
(Continued)

*Primary Examiner* — Hayden Brewster
(74) *Attorney, Agent, or Firm* — Gavrilovich, Dodd & Lindsey LLP

(57) ABSTRACT

The present invention relates to a method for filtering blood to produce plasma or serum and to a blood filter for the production of plasma or serum from a blood sample. The invention further relates to a kit comprising a blood filter for the production of plasma or serum from a blood sample and a syringe.

11 Claims, 12 Drawing Sheets

Figure 1:
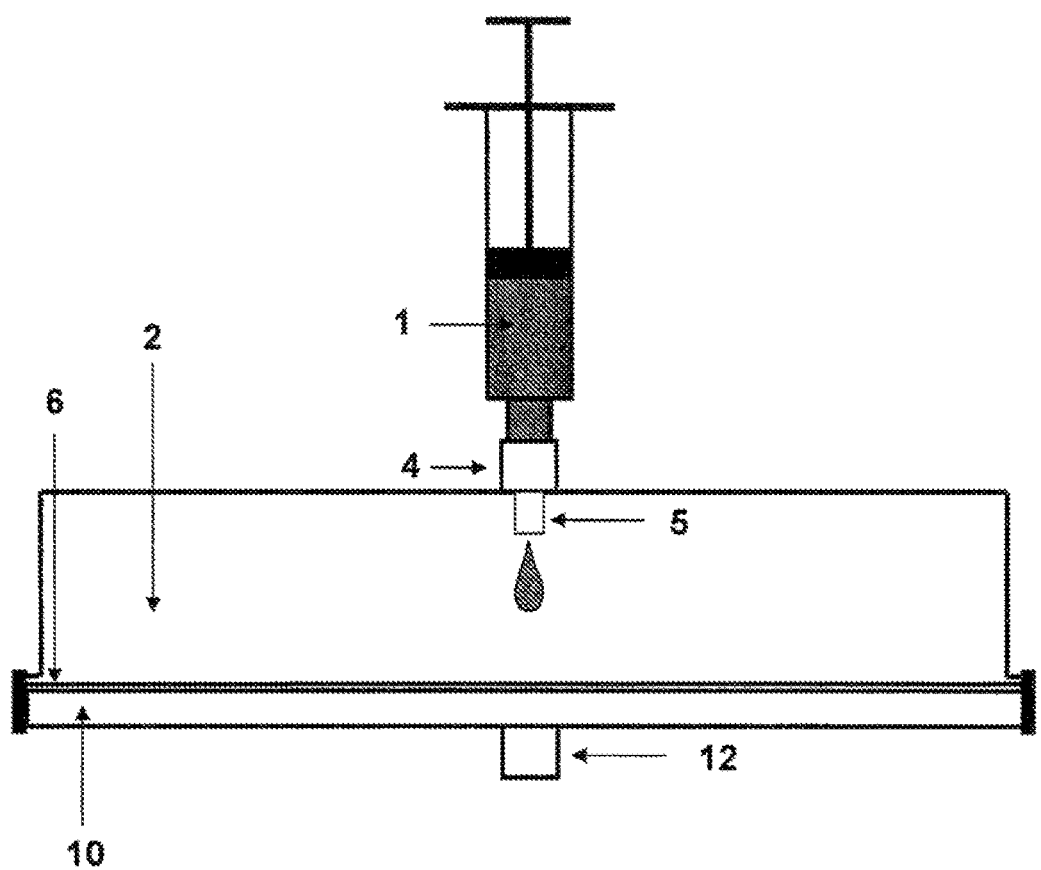

(51) Int. Cl.
*B01D 63/08* (2006.01)
*G01N 33/49* (2006.01)
*B01D 11/00* (2006.01)
*C02F 1/44* (2006.01)

(52) U.S. Cl.
CPC ... *G01N 33/491* (2013.01); *A61M 2205/3331* (2013.01); *B01D 2313/10* (2013.01)

(56) References Cited

U.S. PATENT DOCUMENTS

| | | |
|---|---|---|
| 4,522,713 A | 6/1985 | Nussbaumer et al. |
| 5,779,676 A * | 7/1998 | Kriesel ................ A61M 5/152 604/132 |
| 6,045,699 A | 4/2000 | Yazawa et al. |
| 6,506,167 B1 | 1/2003 | Ishimoto et al. |
| 2007/0105156 A1 | 5/2007 | Togawa et al. |

FOREIGN PATENT DOCUMENTS

| | | |
|---|---|---|
| EP | 0893130 A | 1/1999 |
| EP | 0893130 A1 | 1/1999 |
| JP | S62-135749 A | 6/1987 |
| JP | H10513259 A | 12/1998 |
| JP | 2007-304016 A | 11/2007 |

OTHER PUBLICATIONS

Steinmetz, Johannes, Office Action issued in European Patent Application No. 10730119.4, European Patent Office, dated Feb. 1, 2013.
Steinmetz, Johannes, extended European Search Report, issued in European Patent Application No. 13168744.4, European Patent Office, dated Jul. 18, 2013.
Steinmetz, Johannes, Office Action issued in European Patent Application No. 10730119.4; European Patent Office, dated Jul. 17, 2013.
Filtration; Aldermaston, Berks; www.taab.co.uk/pdf-details/6_taab_sections_1204015523.pdf; p. 4.3-4.7; Aug. 13, 2008.
"Membrane Separation Technology for Research and Quality Control", Sartorius Separation Technology, Mar. 1997, p. 1-30.
Li Jinjin, Office Action issued in Chinese Patent Application No. 201080026906.0, China State Intellectual Property Office, dated Nov. 5, 2013.
Hase, Ushio, Office Action issued in Japanese Patent Application No. 2012-515497, Japanese Patent Office, dated Oct. 29, 2013.
Steinmetz, Johannes, Communication Pursuant to Article 94(3) EPC issued in European Patent Application No. 13168744.4, European Patent Office, dated Apr. 10, 2014.

* cited by examiner

METHOD FOR FILTERING BLOOD TO PRODUCE PLASMA OR SERUM

CROSS REFERENCE TO RELATED APPLICATIONS

This application is a divisional of U.S. patent application Ser. No. 13/378,991, having a filing date of Jan. 30, 2012, which is a U.S. National Stage Application filed under 35 U.S.C. § 371 based upon International Application No. PCT/EP2010/058551, filed Jun. 17, 2010, which application claims priority to European Application No. 09163006.1, filed Jun. 17, 2009, the disclosures of which are incorporated herein by reference in their entirety.

DETAILED DESCRIPTION

The present invention relates to a method for filtering blood to produce plasma or serum and to a blood filter for the production of plasma or serum from a blood sample. The invention further relates to a kit comprising a blood filter for the production of plasma or serum from a blood sample and a syringe.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The filtration of blood to separate solid blood components from serum or plasma is a necessary step to enable for the determination of the presence and/or concentration of compounds dissolved in the blood starting from serum or plasma. By now, most filtration methods rely on a centrifugation step and no feasible alternative methods have been suggested so far. However, centrifugation is time consuming and poses problems in particular in developing countries since the institutions there often lack suitable centrifuges and therefore cannot carry out the essential step necessary to obtain the basis material for determining the presence and/or concentration of compounds dissolved in the blood.

Membranes for filtering blood in order to obtain plasma or serum have been recently developed and are disclosed, e.g., in U.S. Pat. Nos. 6,939,468 and 7,125,493. However, no device has been developed yet which enables for the rapid production of serum or plasma without a centrifugation step.

Hemolysis, i.e., the destruction of red blood cells leading to the liberation of haemoglobin, is an unwanted side effect in many techniques for blood filtration. It usually occurs if the pressure applied is too high, which leads to excessive pressure difference and shear force destroying erythrocytes. Hemoglobin, however, interferes with many uses of plasma or serum so that hemolysis should be avoided in the production of serum or plasma.

Therefore, there is a need for a device and/or method enabling for producing serum or plasma for further analysis without centrifugation and without hemolysis. Such a device and/or method should furthermore or alternatively be cost effective.

Accordingly, the present invention relates to a method for filtering blood to produce plasma or serum, comprising the steps of:

a. providing a blood filter comprising a filter membrane having opposite first and second sides and a receiving compartment defining a hollow space; and
b. inserting a blood sample into said receiving compartment, wherein the volume of said hollow space is 3 to 20 times larger than the volume of said blood sample, thereby increasing the gas pressure within said receiving compartment, preferably to force said blood sample against said filter membrane, so that said blood sample is filtered by said filter membrane, and wherein said plasma or serum comprised in said blood sample is forced through said filter membrane.

The term "plasma" relates to the liquid phase of the blood obtained after separation of its solid constituents such as cells (leukocytes, erythrocytes etc.) which can still coagulate.

The term "serum" relates to the liquid fraction of blood which is obtained after coagulation of the blood by separation of the cruor formed by the cellular constituents of the blood, thrombocytes and coagulation factors.

Depending on the filter membrane used, the serum or plasma obtained from the blood filter of the invention may still comprise at least a part of the thrombocytes comprised in the blood applied to the filter. Whether this is the case depends, inter alia, on the filter membranes used.

The filter membrane comprised in the blood filter of the invention is suitable to filter blood in order to obtain plasma or serum. Membranes for filtering blood in order to obtain plasma or serum have been recently developed and are disclosed, e.g., in U.S. Pat. Nos. 6,939,468 and 7,125,493. Suitable filter membranes may comprise, e.g., polyethylene terephthalate (such as available, e.g., from Sekisui in a product for the production of serum) or polysulfone (such as the Vivid Plasma Separation Membrane available from Pall).

A blood sample is a sample comprising blood of an individual. Individuals comprises any animal which uses blood for the transportation of oxygen and/or nutrients. Preferably, the individual is a human.

The present inventors have surprisingly found that a distinct assembly of features in a blood filter and/or the application of distinct features in a method enables for the rapid production of serum or plasma for further analysis with substantially no hemolysis. A principle underlying the present invention is the ratio of the volume of the hollow space in front of the filtering membrane and that of the blood to be filtered which is preferably between 3:1 and 20:1. This ratio has been found to be beneficial to enable to separate blood without hemolysis based on pressure applied. It is based, in part, on the construction of the blood filter of the invention, the surface of the filter membrane and its resistance for air. In accordance with the invention, a volume of blood is filled into the receiving compartment in a way that the gas within said compartment is compressed thus rising the pressure in said receiving compartment.

The present method/device is based on a blood filter comprising a filter membrane having opposite first and second sides and a receiving compartment, wherein said receiving compartment preferably is one inseparable piece. Exemplary blood filters applicable in the method of the invention are depicted in FIGS. 1, 3, 5, 7, 9 and 10.

In the present method, a blood sample having a defined volume is filled into an insertion means, such as a syringe or a pipette. Preferably, the insertion means only comprises said blood sample and, preferably substantially, no air or other compressible gas. In other words, said syringe or pipette is preferably filled with said blood sample only. Said insertion means is then attached to the receiving compartment of said blood filter, either directly or via an adapter, so that both are in fluid communication. The plunger of said insertion means is then pressed down thereby inserting the blood sample into the receiving compartment. Thereby, the internal pressure within said receiving compartment will be increased to reach a stable magnitude. Said stable magnitude will usually be reached immediately after the blood sample has been inserted into the receiving compartment and preferably covers said filter membrane. Prior to covering, a small amount of air or other gas which is comprised in said receiving compartment will run through the pores of said filter membrane. Therefore, it is envisaged that the blood sample be inserted rapidly into said receiving compartment, preferably such that it, preferably also rapidly, covers said filter membrane. In this regard, "rapidly" comprises a time of between 0.5 and 5 s, preferably between 0.5 and 3 s, until the filter membrane is covered which may result in a loss of about 1/20 to 18/20 of the air or other gas comprised in said receiving compartment.

The increased internal pressure obtained after coverage of the filter membrane with the blood sample forces the solid components of the blood sample against and, at least in part, into and the serum or plasma through said filter membrane so that it may be collected on the second side of said filter membrane located on a sampling compartment while remaining components of the sample remain in the filter medium.

The pressure applied to the receiving compartment is in fact a pressure difference of the internal pressure as compared to the pressure surrounding the filter. The resulting internal pressure after inserting the blood sample and coverage of the filter membrane by said blood sample is preferably essentially constant. This may be achieved by holding down the plunger of the insertion means but in many cases also by simply relieving the plunger. This is because the pressure applied as compared to the surrounding pressure is so low that the resistance of the plunger within the insertion means, e.g., the syringe, is so high that it will remain at the position that it had after pressing it down. Alternatively, the syringe may further comprise a means to lock the plunger at the desired position. Additionally or alternatively the opening of the receiving chamber into which the sample is provided is a one way valve.

The present invention also relates to a method for filtering blood to produce plasma or serum, comprising the steps of:

a. providing a blood filter comprising a filter membrane having opposite first and second sides and a receiving compartment having a first volume;

b. inserting a blood sample and a gas into a syringe, the blood sample occupying a second volume and the gas occupying a third volume in the syringe;

c. connecting said syringe to said blood filter to be in fluid communication with each other; and d. increasing the pressure within said syringe, preferably due to pushing the plunger until the blood sample is received by said receiving compartment, preferably by at least 1/20 of the third volume, preferably between 1/20 and 4/20 and preferably about 2/20, beyond the point of equalized pressure inside and outside of the blood filter, i.e., inside the syringe and inside the receiving compartment, thereby preferably forcing said blood sample against said filter membrane, so that said blood sample is filtered by said filter membrane, wherein said plasma or serum comprised in said blood sample is forced through said filter membrane.

It may be preferable that the sum of first and third volume is 3 to 20 times larger than the second volume, under ambient pressure.

For this embodiment as well as the other embodiments of the present invention described further below, the explanations and definitions given for the blood filter of the invention are applicable since the principles underlying the blood filter of the invention and the method of the invention are substantially the same. This does not exclude that means and blood filters other than that according to the invention may be used in the method of the invention.

In this alternative or additional embodiment, the first volume formed by the receiving compartment is comparably small and preferably approaches zero. The present method is also based on a ratio of volumes which, in this case, is that between the first and third volume formed by the syringe and the receiving compartment and the narrowing volume which is the volume along which the plunger is pushed beyond the point of equal pressure inside and outside of the blood filter, i.e., inside the syringe and inside the receiving compartment. This narrowing amount is about 1/20-4/20 of the third or gas volume. After inserting the blood sample and the appropriate volume of gas into the syringe, said syringe is connected to said blood filter to be in fluid communication therewith. This means that said syringe may be directly attached to said filter or that both may be connected via an adapter or a tubing which preferably has only a small dead volume. After the connection has been established, the pressure within said syringe is increased until the blood sample is received by said receiving compartment. This is preferably effected in a way that, prior to any gas entering the receiving compartment, said blood sample is received by said receiving compartment. More preferably, during pressure increase, the syringe is held down so that the blood enters said receiving compartment first. The syringe may further comprise a means to arrest the plunger at the desired position. As described above, the internal pressure within said receiving compartment will usually be increased immediately after the blood sample covers said filter membrane. Prior to covering, an amount of air or other gas which is comprised in said receiving compartment will run through the pores of said filter membrane. Therefore, it is envisaged that the blood sample be inserted rapidly into said receiving compartment. Upon the pressure increase after the filter membrane being covered with said blood sample, said blood sample is forced into said filter membrane and plasma or serum comprised in said blood sample through said filter membrane, as also discussed above.

For example, using a blood filter described above, a volume of blood is to be filled into a syringe as well as a volume of air, preferably being about 3-20 times the volume of the blood. After connection to the filter the plunger has to be pushed to a certain extent, e.g., depending on the actual blood filter characteristics. When the receiving compartment is filled with blood and the membrane is all wet, preferably a point of equalized pressure inside and outside of the blood filter, i.e., inside the syringe and inside the receiving compartment is reached. Then, further pushing of the plunger leads to a pressure increase compressing the air in the syringe by at least 1/20 up to about 4/20 of the volume of air inside the syringe.

Due to loss of gas through the filter until the complete filter is wetted with blood, the resulting compression of gas is less than the practically applied compression. The effective compression is between 1/20 and 4/20 (typically 2/20, blood/gas respectively), resulting in a pressure increase of about 5-20 kPa. The practical ratio of the volumes of gas and blood is between 3:1 and 20:1. The exact ratio applied depends on the time needed until the membrane is wetted and the loss of gas until then. The loss of gas again depends on the resistance of airflow of the membrane as well as that of the capillaries until the gas passes the outlet.

Using filter membranes such as the Pall Vivid membrane, typically a sample volume of ca. 100 µl (minimum of 25-35 µl/cm$^2$ filter membrane, maximum 600 µl/cm$^2$ filter membrane) blood per cm$^2$ filter-membrane is sufficient in order to obtain an amount of serum or plasma sufficient to carry out most diagnostic evaluations. The surface of the filter membrane is not limited, but would in practical terms be preferably at least 1 cm$^2$. Commonly applied surfaces of the filter membrane would preferably be between 2 and 20 cm$^2$, preferably between 3 and 10 cm$^2$.

On the example of a membrane of 6 cm$^2$ and a blood sample of ca. 600 µl, the membrane will be all wet in between 1 and 5 seconds. If a porous sheet on top of the membrane is used as will be described further below, the wetting time can be shortened such that the membrane will be wet within 0.5-3 seconds. If a disc to channel the blood is used, as also described further below, the delay between the application of blood and wetting the membrane is approaching the time needed to fill the blood into the blood filter. If blood in excess (150-600 µl/cm$^2$ filter membrane) is used, the wetting time is also considerably shorter. After filling, the filtration starts. It takes typically 20-60 seconds until the filter is blocked due to erythrocytes. Using 6 cm$^2$ of the pall membrane, an output of 60-120 µl plasma could be obtained.

In another preferred embodiment the filter comprises an outlet which is closed during the filling with blood and opened after the membrane is fully wet. Such a blood filter will need a volume ratio between 20:1 and 20:4 (gas/blood) only.

The pressure arising from the gas being compressed, which effectively is the pressure difference of the gas pressure in the filter prior to applying the blood sample (usually atmospheric pressure) and after wetting the filter membrane with blood is necessary and sufficient to force the blood applied into the filter membrane the porous structure of which provides the only escape for gas and/or liquid to relieve said pressure. In said filter membrane the cellular components of the blood, in particular red and white blood cells, but also thrombocytes if desired, are separated from the liquid fraction which is serum or plasma, depending on whether an anticoagulant had been added to the blood prior to filtration or not. The defined ratio of the volume of the receiving compartment and the blood sample leading to a defined pressure within said receiving compartment thus largely prevents that an overpressure is created which results in hemolysis.

According to the invention, the volume of the hollow space of said receiving compartment is between 3 and 20 times larger than the volume of the blood sample to be filtered. Preferably, corresponding to the first embodiment of the invention the volume of said hollow space is between 3 and 6 times larger, exemplified on a blood filter according to FIGS. 1, 5 and 9, or between 3-8 times larger exemplified on a blood filter according to FIGS. 3, 7 and 10 than the volume of the blood sample to be filled in the blood filter. The blood filled into the receiving compartment will wet the membrane and compress the air inside the receiving compartment which is preferably resulting in an effective compression rate of 4/20-1/20 of the second and/or third volume (pressure of about 5-20 kPa difference to ambient) including the loss of air through the membrane before completely wet.

Preferably, and corresponding to the second embodiment of the invention the compression rate of the gas, which volume is preferably 3-20 times larger than the volume of blood in the syringe, exemplified on a blood filter according to FIGS. 2, 4, 6, and 8, is preferably between 4/20-1/20 of the second volume plus the volume of the receiving compartment to be filled, i.e., the third volume. Practically, the volume narrowing in the syringe using the plunger is a little more than indicated above accounting to the loss of gas through the membrane until fully wet, and is preferably about 2/20-6/20 of the sum of the volume of the gas and the volume of the receiving compartment.

In both embodiments the gas volume is narrowed in the range of 1/3-1/20, preferably resulting in a working pressure difference of about 5-20 kPa because of some loss of air.

In a preferred embodiment, the method further comprises the step e) of compressing the first and third volume by pressing down the plunger of said syringe beyond a position where the blood sample is received by said receiving compartment, preferably wherein a time lag is provided between steps d) and e).

This additional step is preferably to be carried out if the volume of gas pressed through said filter membrane prior to the filter membrane being completely covered with the blood sample is more than 3/20.

In another preferred additional or alternative embodiment of the methods according to the invention, said receiving compartment has at least one opening covered with said first side of said filter membrane.

The opening comprised in said receiving compartment is at least partially covered with said first side of said filter membrane. Preferably, the opening is fully covered with said first side of said filter membrane. In any case, the opening, if not fully covered with said first side of said filter membrane, is covered with a different material to the extent that it is not covered with said first side of said filter membrane. In other words, if said opening is not fully covered with said first side of said filter membrane, the remaining part of the opening is covered with a different material. Such material may comprise a ring-like structure arranged at the boundary of the receiving compartment to fix said filter membrane.

The filter membrane covers the opening comprised in said receiving compartment and preferably separates said receiving compartment from said sampling compartment, preferably such that the first side of said filter membrane faces towards the receiving compartment.

The present invention also relates to a blood filter for the production of plasma or serum from a blood sample, preferably according to the method underlying the invention, comprising: a filter membrane having opposite first and second sides; a receiving compartment defining a hollow space for receiving a blood sample to be filtered, said receiving compartment having at least one opening covered with said filter membrane, wherein said first side of said filter membrane is facing said receiving compartment, and wherein the hollow space of said receiving compartment has a volume being 3 to 20 times larger than the volume of the blood sample to be filtered; and a sampling compartment being arranged on said second side of said filter membrane.

In a preferred embodiment of the methods or the filter of the invention, the volume of said hollow space or the sum of said first and third volume is at least 0.3 ml.

Common volumes of said hollow space or the sum of said first and third volume are between 0.3 and 30 ml, depending on the surface of the filter-membrane, preferably between 1.5 and 25 ml, more preferably between 2 and 15, such as 3, 4, 5, 6, 7, 8, 9, 10, 11, 12, 13, 14 ml and any value in between these values.

The pressure suitable to filter blood to produce serum or plasma should preferably lie between 5 and 20 kPa. A pressure of about 10 kPa is generated if a gas such as air is compressed by 1/10 of its volume. With these features, a syringe can be constructed the plunger of which can move only corresponding to, e.g., 1/10 of its entire volume.

Using this kind of system for obtaining blood and filling that the blood into the filter blood filter according to FIGS. 2, 4, 6 and 8, the correct pressure applied for a sufficient amount of time leads to a sufficient amount of plasma or serum.

In another preferred embodiment a pipette can be used instead of a syringe, especially for small volumes.

In a preferred embodiment of the methods or the filter of the invention, said receiving compartment is made from a material that is adapted to withstand a pressure difference of at least 7 kPa, preferably at least 18 kPa, more preferably at least 30 kPa without substantial deformation.

In another preferred embodiment of the method or the filter of the invention, said receiving compartment is made from a substantially inelastic and/or rigid material, which inelasticity or rigidness may also be achieved based on the thickness or the material used. Exemplary materials are inelastic plastics, like polycarbonate, polystyrol, polvinylchloride, polyethylene, polypropylene, polyurethane, polyethersulfon and mixed compounds etc.

It is further preferred that, preferably in addition to said receiving compartment, said sampling compartment is made from a material that is adapted to withstand an internal pressure of at least 7 kPa, preferably at least 18 kPa, more preferably at least 30 kPa without substantial deformation.

Alternatively or in addition to the above definition of the material of the receiving and/or sampling compartment, the volume of the receiving and/or sampling compartment is not enlarged by more than 10%, preferably 5%, more preferably 1% upon application of a pressure between 6 and 25 kPa.

In a preferred embodiment, said receiving compartment and said sampling compartment, prior to use, are filled with a gas, preferably air, under atmospheric pressure.

Suitable gases other than air comprise commonly applied gases such as inert gases (argon, helium, neon), nitrogen or carbon dioxide.

A further preferred feature of the blood filter of the present invention is that at least 50% of the surface of the second side of the filter membrane is covered. In this regard, the term "covered" relates to the direct contact of one material, e.g., the filter membrane, with another material, e.g., another substrate comprised in the sampling compartment. In the course of the present invention, it was surprisingly found that the coverage of the second side of the filter membrane to a certain extent, such as at least 50%, promotes the yield of serum or plasma from the filtration process. Preferably, said serum or plasma is channeled towards the outlet of the blood filter to be collected. The efficiency of the filtration process increases with the percentage of the filter membrane covered. This feature is minimizing the dead space as well. This apparently contradictory result is not obtained if fluids other than blood, e.g., water, are used. Such other fluids would rather require as much free space in the outlet chamber in the direct vicinity of the filter membrane as possible.

In another preferred embodiment, at least 50%, preferably at least 75%, more preferably at least 90%, and most preferably at least 95% of the surface area of the second side of said filter membrane is covered.

In a more preferred embodiment, the second side of the membrane is in contact with a substantially flat substrate, wherein said flat substrate is preferably part of the sampling compartment.

The term "substantially flat" comprises surfaces which may be completely flat, i.e., without any elevations or indentations in the range of about 5-1000 µm, but also surfaces, wherein at least 80%, preferably at least 90%, more preferably at least 95% are flat and also surfaces with elevations or indentations of less than 1 mm height. The term also encompasses structures comprising more than one flat area arranged in an angle or a curved, e.g., convex or concave configuration, laying flat on the filter and preferably relates to material which is adapted to lay flat on or against the second side of the filter. In other words, the dead space between filter membrane and the supporting and draining flat substrate should not exceed 5 µl per cm$^2$ filter membrane surface, therefore most of the membrane is preferably in contact with the substrate.

This preferred embodiment takes into account that small channels in the blood filter leading to a place where the plasma or serum can be collected may to a certain extent promote the yield of serum or plasma. If present, said channels preferably lead to an outlet comprised in said sampling compartment. However, a further surprising effect of the present invention is that generally the larger the part of the filter membrane being in contact with said substantially flat surface, the better is the yield of serum or plasma.

In a preferred embodiment of the methods or the filter of the invention, the blood filter further comprises a hydrophilic and porous sheet arranged on the first side of said filter membrane in said receiving compartment which is preferably covering said filter membrane, wherein said porous sheet is preferably made of fibrous material.

Suitable sheets are filter paper (such as used in teabags), nonwoven fabrics (sheet or web structures bonded together by entangling fiber or filaments) made of cellulose or plastic which is made hydrophilic.

A hydrophilic and porous sheet according to the invention serves for rapidly and more evenly distributing the blood to be filtered over preferably the whole surface of the filter membrane. Furthermore, said sheet prevents that mixtures of gas with serum or plasma are obtained from the filtering process which would pose the potential danger of obtaining unwanted foams. The sheet is arranged on the first side of said filter membrane facing the receiving compartment, wherein the filter membrane may be in direct contact with said sheet or be arranged in a distance of up to 1.5 mm, such as 0.5, 0.75, 1 or 1.25 mm. Suitable pore sizes are, e.g., pore sizes larger than 20 µm, such as 50 µm, 100 µm, 200 µm, 500 µm or 1000 µm. These pore sizes enable for the rapid suction of the blood into the thin layer due to capillary forces and its subsequent entry into the filter membrane due to the increased pressure resulting from the compressed gas. Furthermore, a part of the cellular constituents of the blood may already be removed from the sample at this stage. The sheet is preferably between 0.1 and 1 mm thin. The term "covering said filter membrane" in the context of this aspect of the invention describes the surface of the sheet as either as large as that of the filter membrane, but also smaller or bigger than the filter membrane. Most common would be surfaces which are at least 80%, preferably at least 90%, more preferably at least 95% as large as that of the filter membrane. Equally preferred are sheets which are up to 10% larger than the filter membrane.

In a preferred embodiment of the first and third aspect of the invention, said receiving compartment comprises a sample insertion means. Said sample insertion means is, e.g., part of the preferred embodiment as depicted in FIGS. 1, 3, 5, 7, 9 and 10. Said sample insertion means enables for the introduction of the blood sample to be filtered into the receiving compartment.

In a more preferred embodiment, said sample insertion means comprises a one-way valve, especially for filters depicted in FIGS. 1, 3, 5, 7, 9 and 10. A one-way valve is especially preferable if the blood is introduced with a means which is subsequently removed such as a syringe. In order to prevent that the internal pressure within the receiving compartment is relieved through said sample insertion means, a one-way valve prevents that gas and/or blood leaks out from said sample insertion means rather than is passed through said filter membrane.

In another preferred embodiment, said sample insertion means comprises a luer-taper. This embodiment can be applied if the blood is introduced with a means which is not subsequently removed, such as a syringe. In this regard, the plunger of the syringe will withstand the pressure of about 5-20 kPa because the plunger is stuck in the tube due to the clamping force of the syringe required to be overcome for moving the plunger. This will be the case with most syringes holding a volume up to 10 ml.

It is preferred that the syringe comprises a means to lock the plunger at the position it has reached after the blood has been introduced into the receiving chamber. This is useful in the case that the plunger of the syringe is sliding very easily.

In another more preferred embodiment of the blood filter of the invention, said receiving compartment comprises a syringe.

In this preferred embodiment of the blood filter of the invention, said hollow space of said receiving compartment is for the most part formed by a syringe, whereas only a small part is formed by the space in the immediate vicinity of the first side of the filter membrane. In this embodiment, said syringe comprises the volume of blood to be filtered as well as the appropriate amount of gas, such as air. For filtering the blood, the plunger of the syringe is pressed and the volume of the syringe is reduced by the volume of the blood sample to be filtered. After that, the plunger of the syringe is preferably fixed at that position in order to ensure that the pressure is maintained and that no overpressure is applied.

In a preferred embodiment of the methods and the blood filter of the invention, said sampling compartment comprises an outlet, preferably a universal adaptor.

Said outlet is preferably compatible with commonly used blood filters for further processing of the serum or plasma, such as detection devices, small vessels or short outlets. A universal adaptor enables for the collection of serum or plasma in more than one different devices for further processing of the serum or plasma.

In another preferred embodiment, the blood filter is disposable.

In another preferred embodiment of the methods and the blood filter of the invention, said receiving compartment comprises a nozzle arranged at said sample insertion means. Said nozzle reaches into the hollow space formed by said receiving compartment and may be of a certain length. It serves for conducting the blood sample in the direction of the filter membrane. Accordingly preferred nozzles may reach into said hollow space up to a mm or a few mm in front of said filter membrane. The latter preferred embodiment is especially suitable if the distance between said sample insertion means and said filter membrane is large such as at least 1 cm and if the volume of blood sample to be filtered is small, such as up to 500 µl using a membrane surface of about 5 cm$^2$.

In a more preferred embodiment, the nozzle is attached to a disc, wherein said disc is arranged on top of said first side of the filter membrane. Said disc is not in direct contact with said first side of said filter membrane but arranged in a distance of between 0.1 mm and 1.5 mm. Said distance may develop primal after pressure is applied. Said disc does not span the whole hollow space but leaves at least one gap for pressure balance. The principle underlying this embodiment of the blood filter and method of the invention is that blood led through the nozzle towards the filter membrane is guided by the disc to be evenly distributed on the filter membrane.

In another preferred embodiment of the methods and the blood filter of the invention, the receiving compartment and/or the first side of the filter membrane further comprises at least one substance which can immobilize at least one cellular constituent of blood, such as erythrocytes, leukocytes or thrombocytes. Suitable substances in this regard are, e.g., antibodies specifically binding to at least one of the above cell types, such as, e.g., anti-human erythrocyte antibodies. Said substances may be present in the form of a powder, attached within said receiving compartment or on said first side of the filter membrane or attached on a tissue comprised in the receiving compartment. Exemplary tissues are Leukogard, distributed by Pall, or LG6. Those leukocyte filters may contain polyester wool which surface is treated in a way, so that leukocytes adhere immediately on the wool. Alternatively or in addition, the filters may comprise antibodies to erythrocytes. Further alternatively, the receiving compartment may comprise a powder comprising heterophilic antibodies which agglutinate erythrocytes. Other suitable compounds for agglutination of erythrocytes may be obtained from yeast cells of *Histoplasma capsulatum* or from pyrogenic silica, wheat germ agglutinin, lectin from seeds of bitter gourd, balsam pear, or *Momordica charantia* or other lectins.

The present invention further relates to the use of the filter of the invention for filtering blood to produce serum or plasma.

In a preferred embodiment of the method of the invention, the blood filter of step a. is the blood filter according to the invention.

The present invention furthermore relates to a kit comprising a blood filter for the production of plasma or serum from a blood sample and a syringe. The blood filter comprises a filter membrane having opposite first and second sides, a receiving compartment defining a hollow space for receiving a blood sample to be filtered from said syringe, and a sampling compartment being arranged on said second side of said filter membrane. Said receiving compartment has at least one opening covered with said filter membrane, wherein said first side is facing the receiving compartment, and wherein the hollow space of said receiving compartment has a first volume. The syringe is adapted to receive a predetermined second volume of blood sample, wherein the first volume is 3 to 20 times larger than the second volume.

The present invention furthermore relates to a kit comprising a blood filter for the production of plasma or serum from a blood sample and a syringe. The blood filter comprises a filter membrane having opposite first and second sides, a receiving compartment defining a hollow space for receiving a blood sample to be filtered from said syringe, and a sampling compartment being arranged on said second side of said filter membrane. Said receiving compartment has at least one opening covered with said filter membrane, wherein said first side is facing the receiving compartment, and wherein the hollow space of said receiving compartment has a first volume. The syringe is adapted to receive a predetermined second volume of blood sample and a predetermined third volume of a gas. Furthermore, the syringe is adapted to compress the third volume by between 1/20 to 1/5 of the third volume According to a preferred embodiment, the first volume of said hollow space or the sum of said first and third volume is at least 0.3 ml.

The receiving compartment is preferably made from a material that is adapted to withstand an internal pressure of at least 7 kPa, more preferably at least 18 kPa, and even more preferably at least 35 kPa without substantial deformation.

Accordingly, the receiving compartment is preferably made from a substantially inelastic and/or rigid material.

According to a preferred embodiment, at least 50%, preferably at least 75%, more preferably at least 90%, and most preferably at least 95% of the surface area of the second side of said filter membrane is covered. It is preferred that the second side of the membrane is in contact with a substantially flat substrate, wherein said flat substrate is preferably part of the sampling compartment.

According to a preferred embodiment, the filter further comprises a hydrophilic and porous sheet arranged on the first side of said filter membrane in said receiving compartment which is preferably covering said filter membrane, wherein said porous sheet is preferably made of fibrous material.

According to a preferred embodiment, said receiving compartment comprises a sample insertion means, which is preferably a one-way-valve. The sampling compartment preferably comprises at least one outlet, preferably a universal adaptor.

It is preferred that the syringe comprises a plunger and a first stop for the plunger of the syringe to stop the plunger during suction or pulling. This minimizes the risk of the plunger being pulled out of the syringe, which in the worst case could lead to spilling the blood sample all over. Furthermore, the first stop can be utilized to determine the third volume. The user may, for example, be told (e.g., by means of an instruction leaflet) to uptake a certain second volume of blood such as 0.5 to 2 ml and to fill up the syringe with a gas, e.g., with air, until the plunger is stopped by the first stop. Thus, the third volume is defined as the inner volume of the syringe minus the second volume loaded with blood.

In addition, the syringe preferably comprises a second stop for the plunger of the syringe to stop the plunger during pushing downwards the plunger within the syringe in order to limit the compression of the third volume. Accordingly, the gas occupying the third volume is compressed by a specific predetermined amount, which results in a predetermined pressure within the third volume which acts onto the blood sample during filtering. Preferably, the first and second stops are arranged such that the third volume is compressed by between 1/20 to 1/5 of the third volume. If standard pressure was present before compression, a pressure of between 1.05 bar and 1.2 bar is achieved, which is sufficient to filter the blood while at the same time sufficiently small to avoid hemolysis.

It is further preferred that the syringe comprises means to arrest the plunger thereof in a predetermined position, preferably in a position after compression of the third volume.

Thus, a user may compress the gas inside the syringe by pressing down the plunger and then arrest the plunger in the preferred position.

The various components of the kit may be packaged in one or more containers.

The present invention further relates to the use of the kit described above for filtering blood to produce serum or plasma.

The present invention furthermore relates to a blood filter for the production of plasma or serum from a blood sample. The filter comprises a filter membrane having opposite first and second sides and a receiving compartment defining a hollow space for receiving a blood sample to be filtered, said receiving compartment being arranged on said first side of the filter membrane. The filter membrane rests on a seating, wherein at least 50% of the surface of the second side of the filter membrane is in contact with said seating, and wherein the seating comprises a plurality of channels for collecting the filtered blood sample. The channels preferably empty out into at least one outlet. According to a preferred embodiment, at least 75%, preferably at least 90% of the surface of the second side of the filter membrane is in contact with said seating.

It is preferred that the seating is convex having a radius of curvature between 30 and 150 mm, preferably between 60 and 100 mm (analogous to a spherical cap). The convex seating may take account of the elongation of the filter material after wetting in order to avoid wrinkle formation. Surprisingly, it has been found that a convex seating or pressure plate increases the filter efficiency in comparison with a substantially flat seating or pressure plate. The convex curvature of the seating inter alia improves the ability of the channels to collect the filtered blood sample and in particular to guide the collected blood sample towards the outlet(s). For this purpose, it is particularly advantageous that the channels are arranged in a grid or web-like structure. Preferably, the ratio of the relative amount of surface comprising channels to the amount of channel-free surface is essentially constant (on a scale of $cm^2$) over, preferably the major area of, the surfaces facing the second side of the filter. Preferably, all or substantially all points with maximum distance to the closest or nearest channel have about the same maximum distance. Furthermore, the total length of all channels should be minimal. Furthermore, there may also be a channeling effect on or within the second side of the filter membrane directed in a direction roughly perpendicular to the filtration flow between first and second side of the filter membrane.

According to a preferred embodiment, the plurality of channels cover between 0.5 and 15%, preferably between 0.5 and 9% of the surface of the seating. The skilled person will understand that the channels are preferably equally distributed over the seating surface to improve the coverage. It is also preferred that two adjacent channels are not further than about 10 mm apart from each other to ensure that blood reaching the seating surface between two channels is collected by one of the channels.

According to a preferred embodiment, the plurality of channels forms a sampling compartment having a volume in the range between 0.06 $mm^3$ and 3.5 $mm^3$, preferably between 0.06 $mm^3$ and 2 $mm^3$ per $cm^2$ of the filter surface.

In the following, the invention is further described on the examples of certain preferred embodiments with reference to the figures. It is to be understood that the figures not only exemplify the blood filter of the invention but also serve to describe the methods according to the invention. Each feature mentioned herein below can equally be adapted and applied to the methods of the invention at the appropriate place, which is immediately clear to the skilled person.

The figures show:

FIG. 1: a sectional view of a preferred embodiment of the blood filter according to the invention with a receiving compartment.

Figure 2:
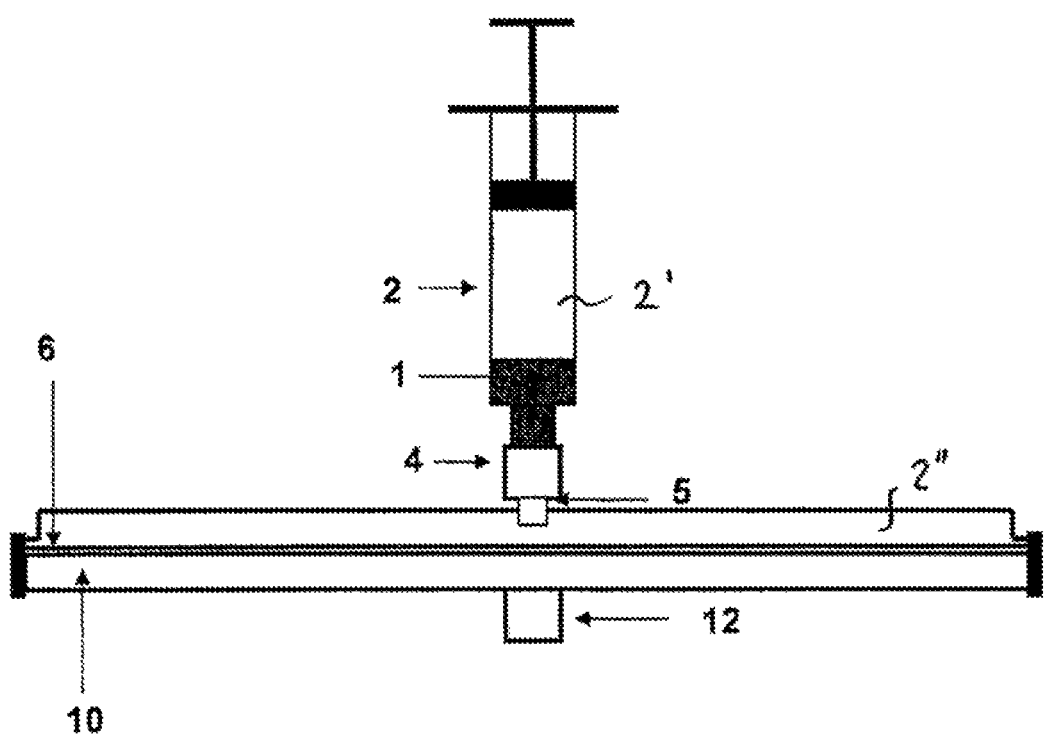

FIG. 2: a sectional view of a preferred embodiment of the blood filter according to the invention with a receiving compartment comprising a syringe.

Figure 3:
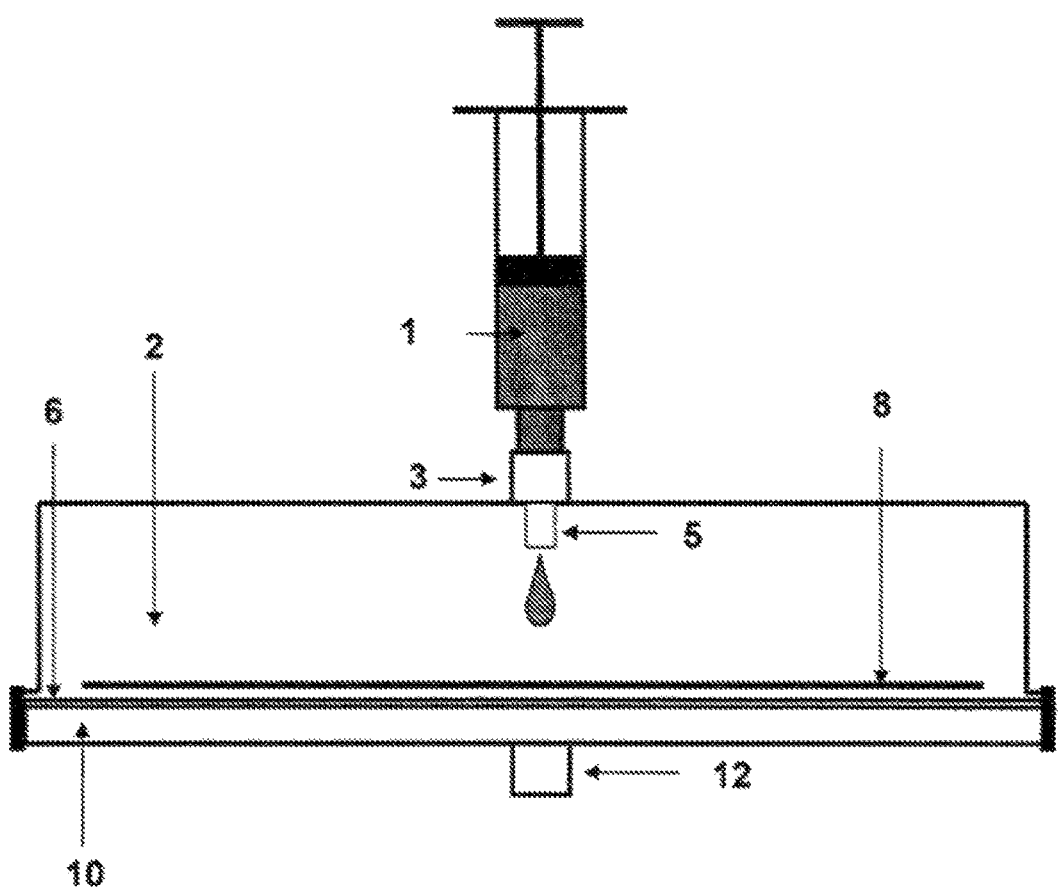

FIG. 3: a sectional view of a preferred embodiment of the blood filter according to the invention with a receiving compartment, wherein the blood filter comprises a hydrophilic and porous sheet on the first side of the filter membrane.

Figure 4:
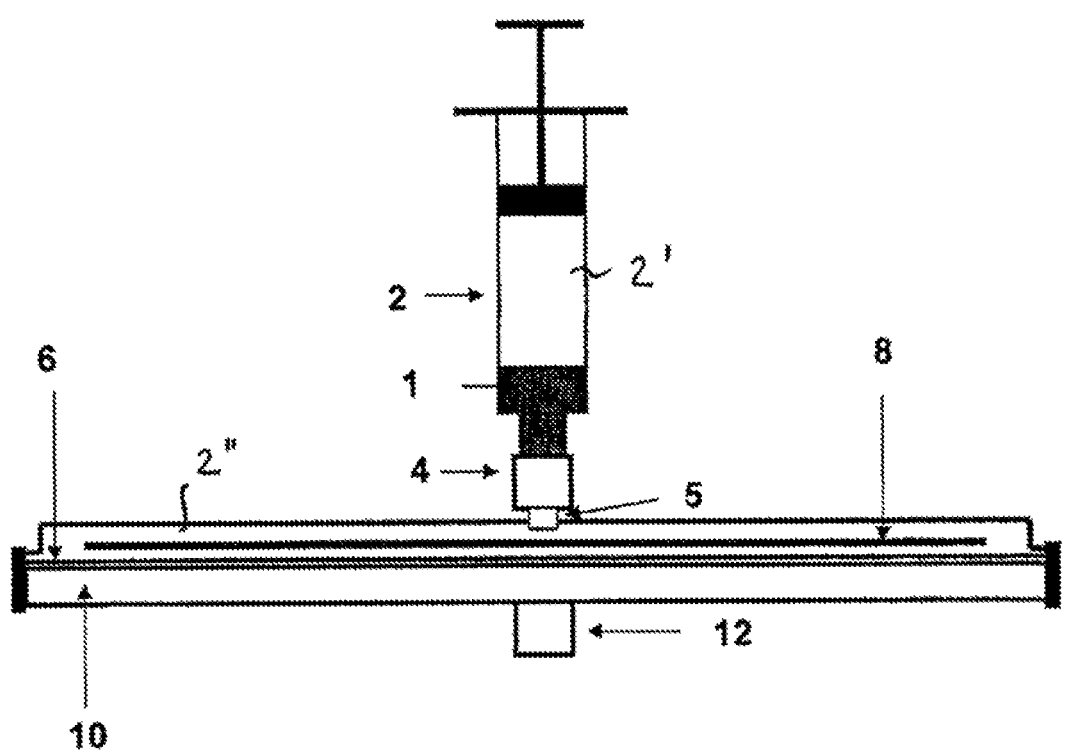

FIG. 4: a sectional view of a preferred embodiment of the blood filter according to the invention with a receiving compartment comprising a syringe, wherein the blood filter comprises a hydrophilic and porous sheet on the first side of the filter membrane.

Figure 5:
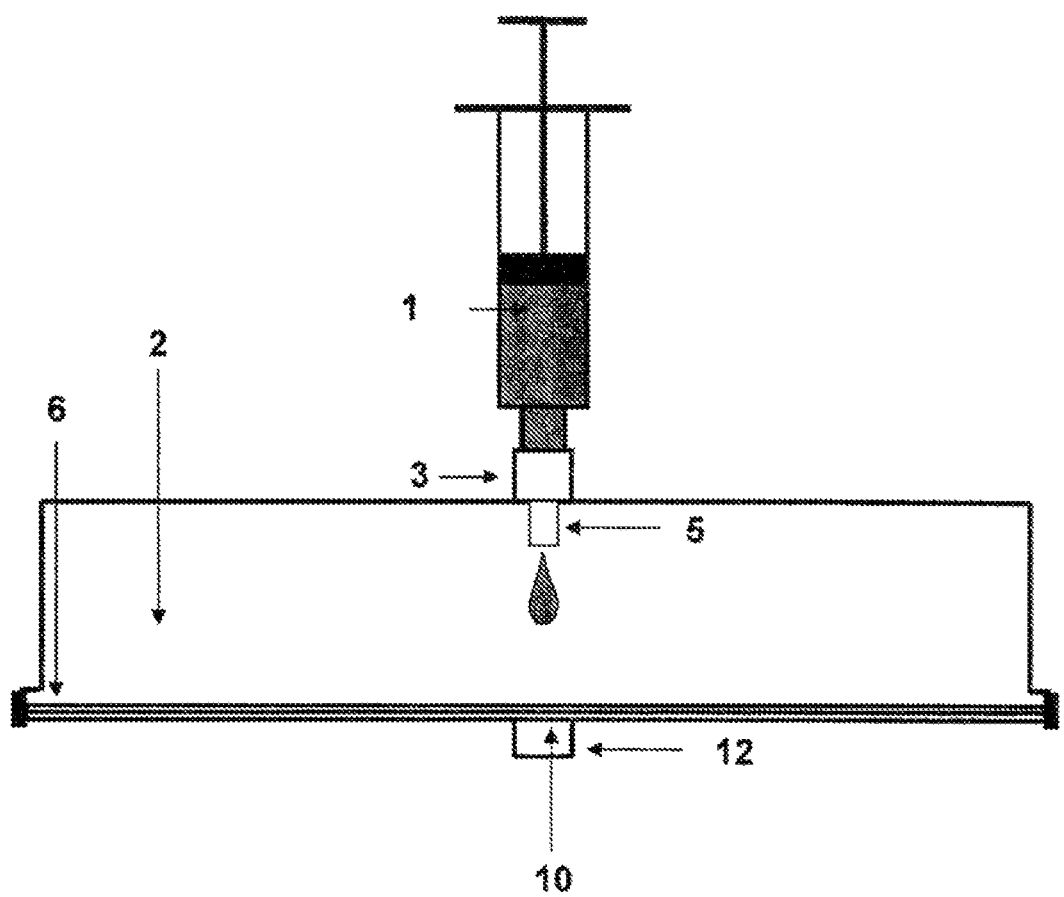

FIG. 5: a sectional view of a preferred embodiment of the blood filter according to the invention with a receiving compartment, wherein at least a part of the second side of the filter membrane is covered.

Figure 6:
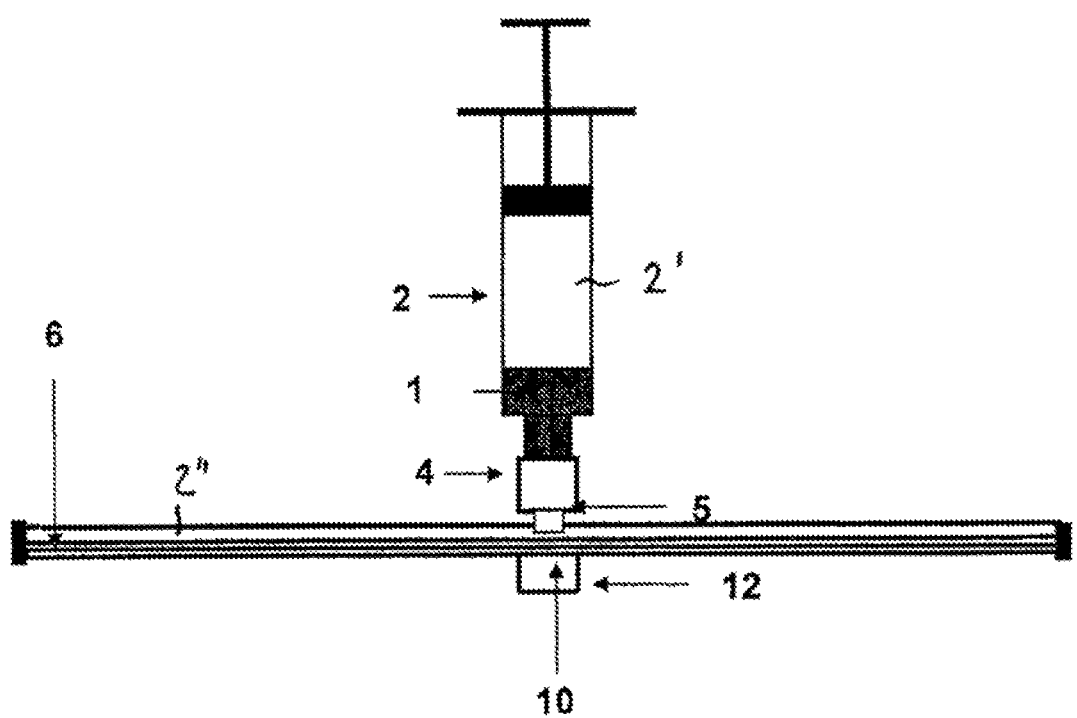

FIG. 6: a sectional view of a preferred embodiment of the blood filter according to the invention with a receiving compartment comprising a syringe, wherein at least a part of the second side of the filter membrane is covered.

Figure 7:
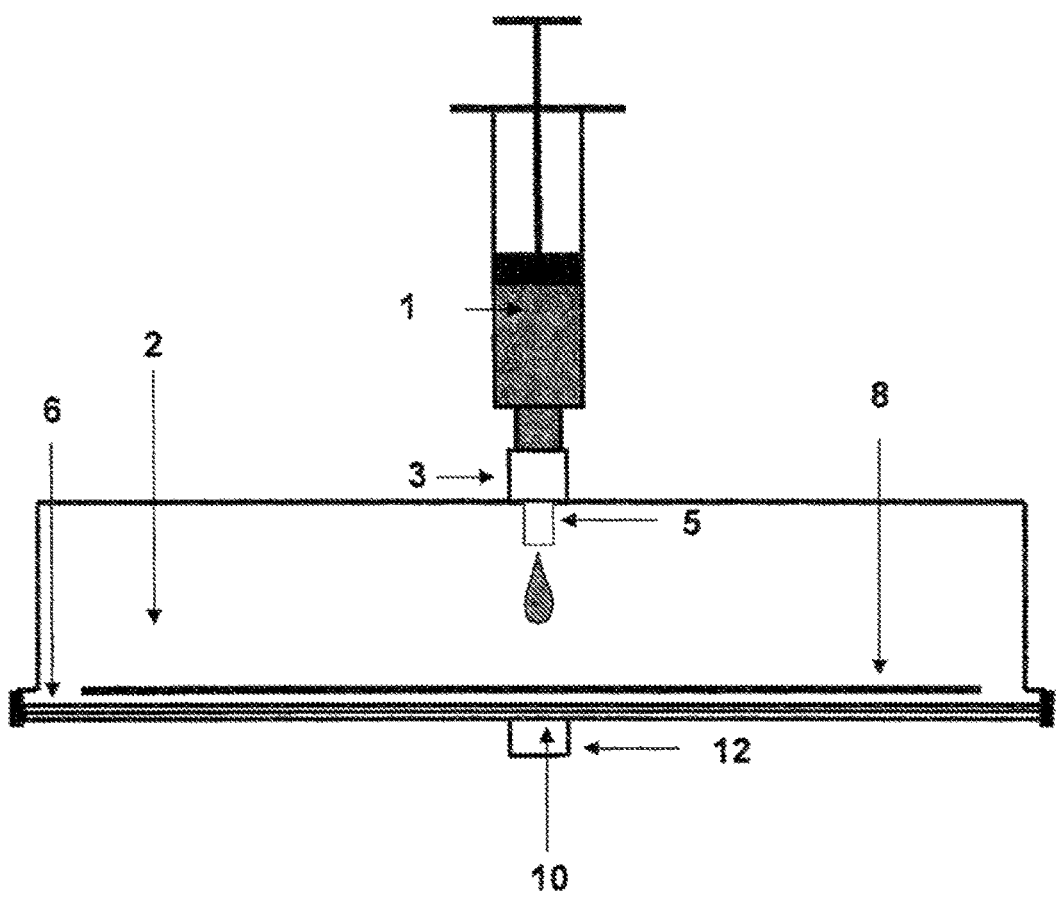

FIG. 7: a sectional view of a preferred embodiment of the blood filter according to the invention with a receiving compartment, wherein the blood filter comprises a hydrophilic and porous sheet on the first side of the filter membrane and wherein at least a part of the second side of the filter membrane is covered.

Figure 8:
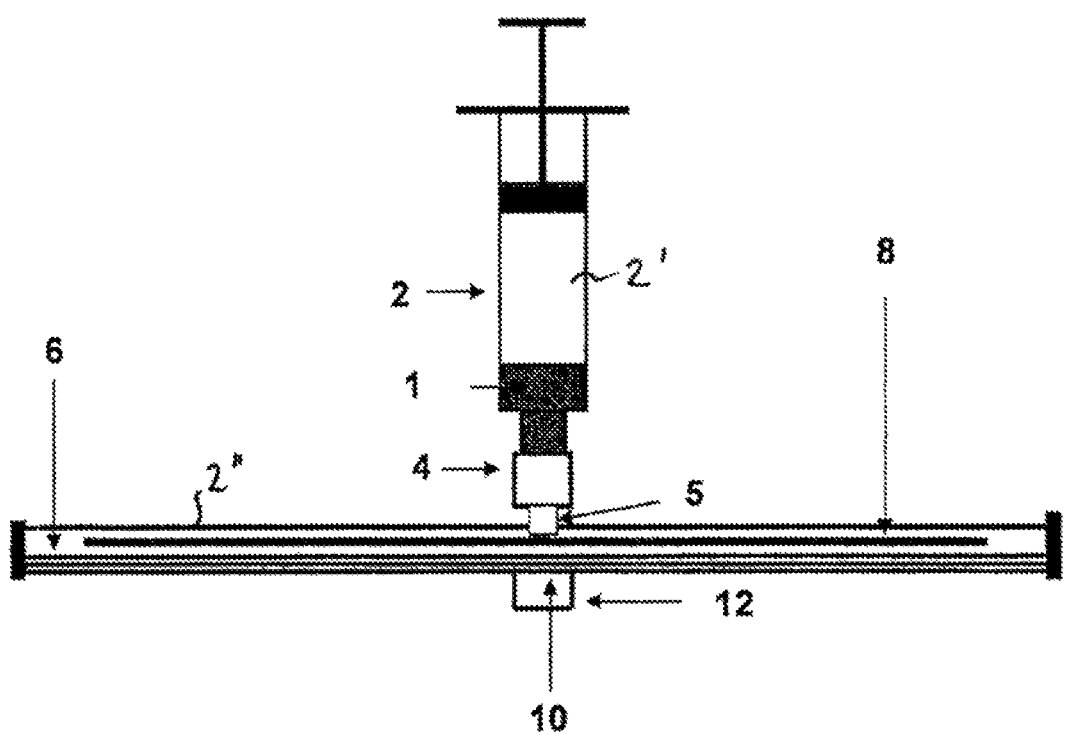

FIG. 8: a sectional view of a preferred embodiment of the blood filter according to the invention with a receiving compartment comprising a syringe, wherein the blood filter comprises a hydrophilic and porous sheet on the first side of the filter membrane and wherein at least a part of the second side of the filter membrane is covered.

Figure 9:
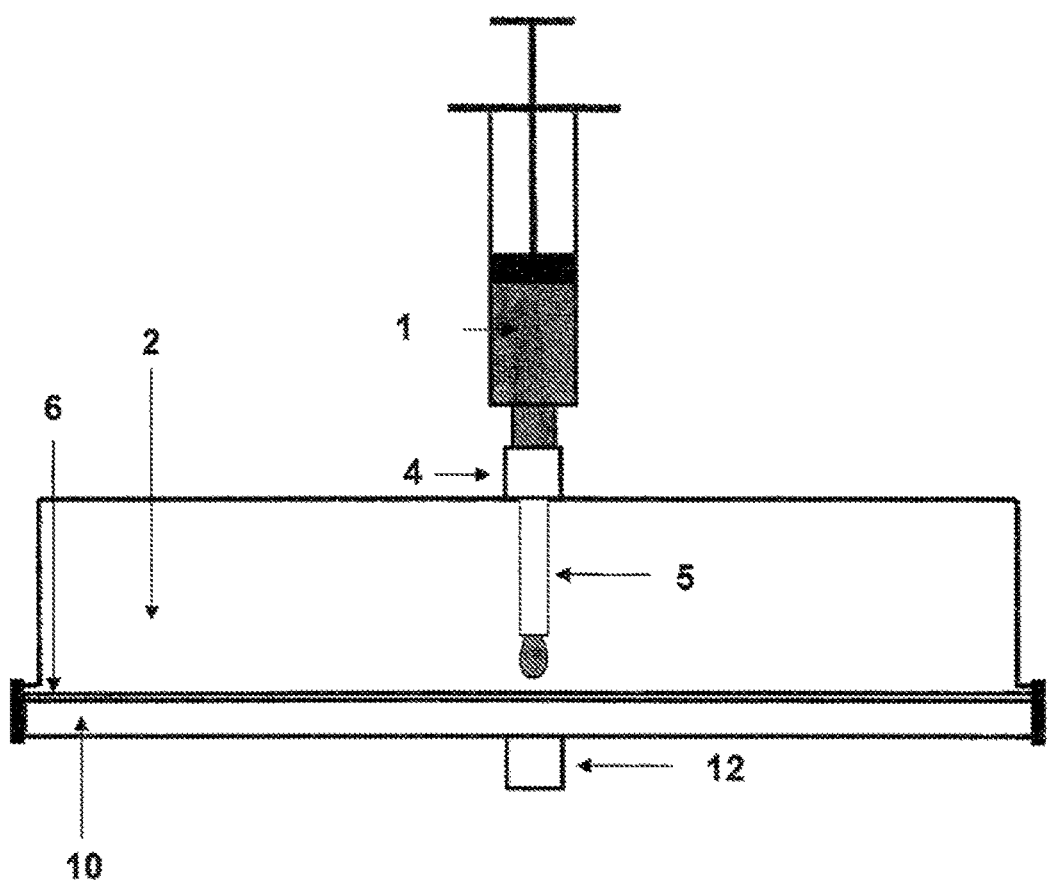

FIG. 9: a sectional view of a preferred embodiment of the blood filter according to the invention with a receiving compartment. The blood filter further comprises a nozzle of variable length.

Figure 10:
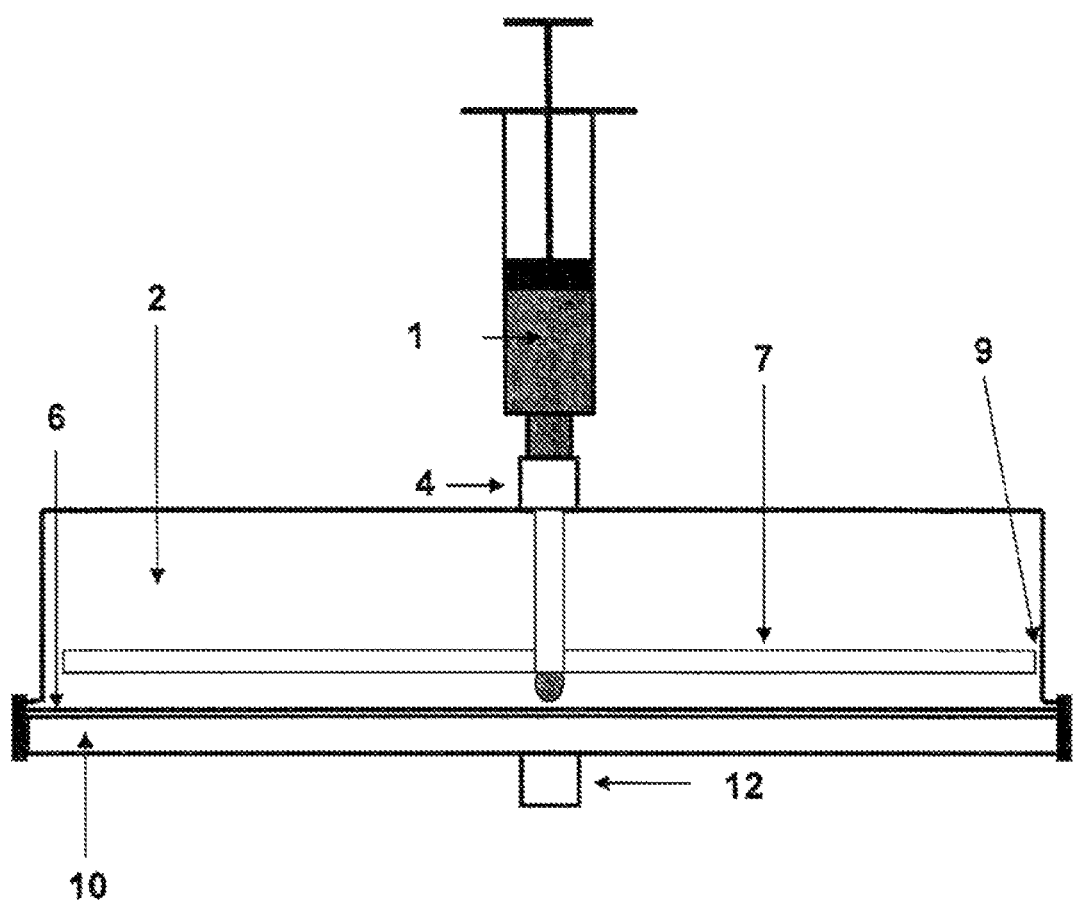

FIG. 10: a sectional view of a preferred embodiment of the blood filter according to the invention with a receiving compartment. The blood filter further comprises a nozzle and a disc attached to the lower end of the nozzle.

Figure 11:
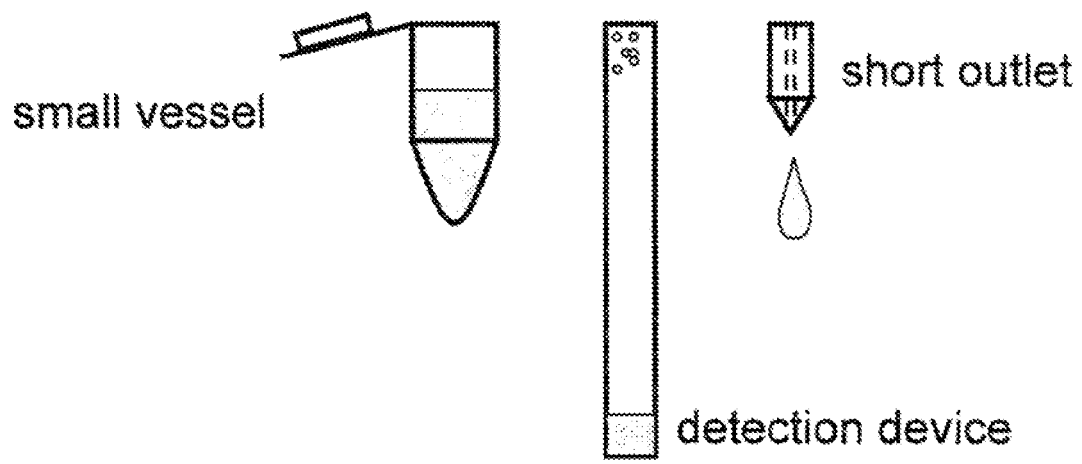

FIG. 11: exemplary outlets or adaptors.

Figure 12:
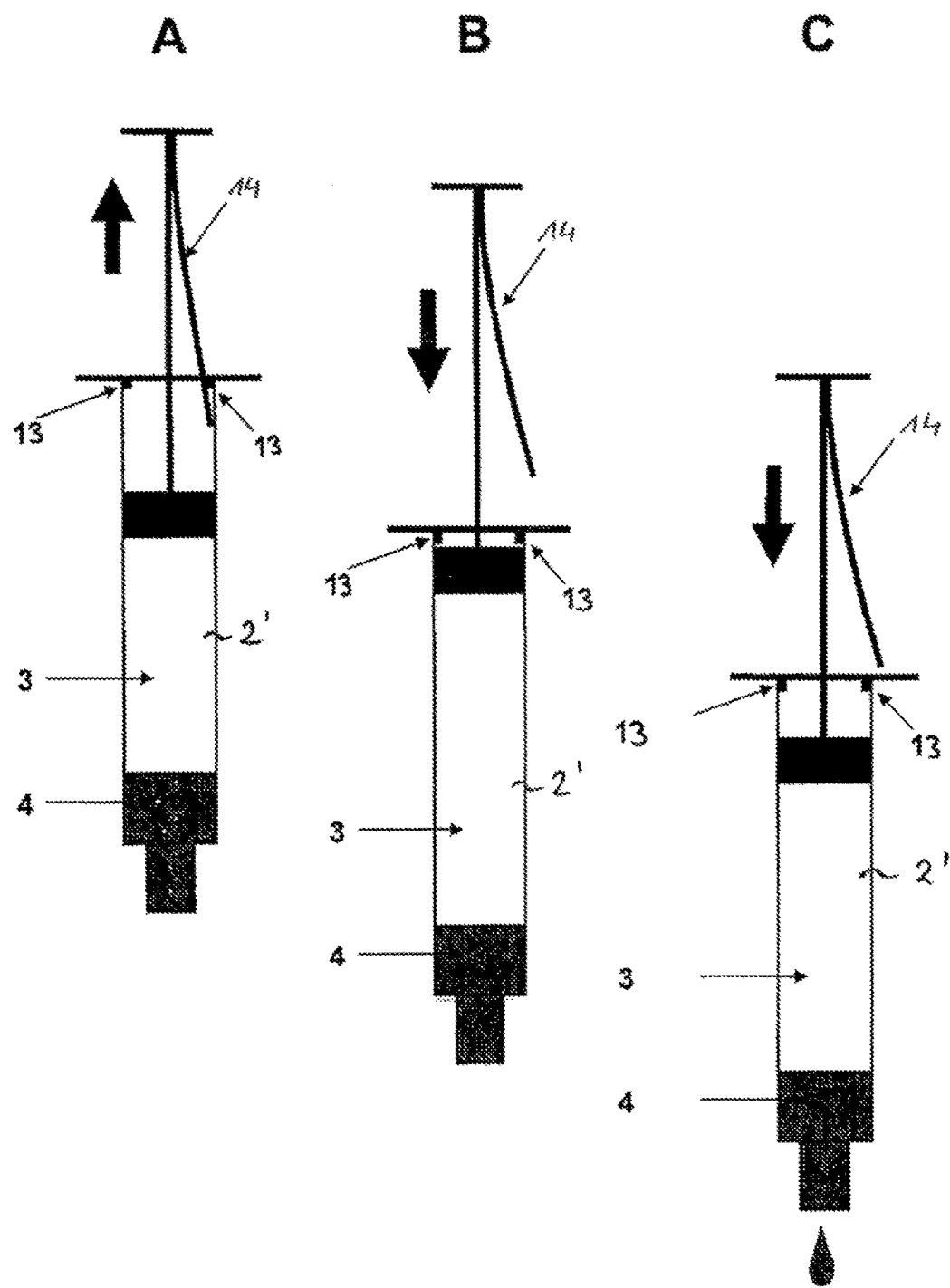

FIG. 12: a sectional view of a preferred embodiment of the syringe to be used with the filter according to the invention with stop mechanisms depicted.

The operating position for the filters according to the present invention, as shown in FIGS. 1-10 is preferably upright with the outlet facing downwards. The deviation of the upright position should not exceed 45 degrees.

A preferred embodiment of the blood filter according to the invention as depicted in FIG. 1 comprises a filter membrane 6 having opposite first and second sides, a receiving compartment 2 defining a hollow space and being arranged on the first side of the filter membrane as well as a sampling compartment 10 arranged on the second side of the filter membrane. The blood 1 to be filtered is introduced by a syringe which is, preferably only, filled with blood and does not or essentially not comprise any gas such as air in its inner space. The syringe is connected to a sample insertion means 3 comprised in the receiving compartment 2. By pressing down the plunger of the syringe, the blood 1 enters the receiving compartment 2 which results in the gas contained in said receiving compartment being compressed which creates a pressure within said receiving chamber. This pressure forces the blood against, into and/or through the filter membrane 6, where, depending on whether the blood has been treated with anticoagulants, solid blood components such as red and white blood cells and optionally thrombocytes are retained, whereas the liquid part of the blood, i.e., serum or plasma, is forced through the filter and enters the sampling compartment 10. The serum or plasma can be collected by having it pass through the outlet 12 for further use.

In this and the other preferred embodiments exemplified in the figures, the receiving compartment 2 is preferably made from a material that is adapted to withstand an internal pressure of at least 7 kPa, preferably at least 18 kPa, without substantial deformation. This means that, more preferably, said receiving compartment is made from a substantially inelastic and/or rigid material.

The blood filter according to the invention as depicted in FIG. 2 comprises a filter membrane 6 having opposite first and second sides, a receiving compartment 2', 2" defining a hollow space, wherein said receiving compartment is in part 2' formed by a syringe, and a sampling compartment 10 arranged on the second side of the filter membrane. In this embodiment, the major part of the hollow space is formed by the syringe comprising the blood 1 to be filtered and a volume of gas 2' under atmospheric pressure which is between 3 and 20 times larger than the volume of blood 1 used to operate the filter. The syringe is removable from the remaining receiving compartment 2" which is especially preferable in order to fill it with the blood to be filtered and a volume of gas as defined above. The thus filled syringe is attached to the remaining receiving compartment 2" via the connector 4 to complete said receiving compartment. By pressing down the plunger of the syringe, the blood 1 is driven to the part of the receiving compartment 2" in the direct vicinity of the filter membrane. This results in the gas contained in the receiving compartment 2" being driven out through the filter membrane and being replaced by blood to be filtered. The gas 2' in the syringe above the blood 1 is compressed because the plunger of the syringe is pressed down for at least 1/20 of the gas volume further after the point of equal pressure inside and outside of the filter. The following processes are similar to those described for FIG. 1. This means that the pressure created forces the blood into the filter membrane 6, where, depending on whether the blood has been treated with anticoagulants, solid blood components such as red and white blood cells and optionally at least a part of the thrombocytes are retained, whereas the liquid part of the blood, i.e., serum or plasma, is forced through the filter and enters the sampling compartment 10. The serum or plasma can be collected by having it pass through the outlet 12 for further use.

In all embodiments of the present invention, the volume of gas or air particularly serves as an elastic buffer and/or pressure reservoir for buffering the pressure applied by the user in order to avoid destruction of erythrocytes by application of too high pressures and for storing and transmitting the pressure applied by the user, e.g., by pushing the plunger, to force or drive the blood sample against the filter membrane.

In general, same reference numerals refer to identical or closely similar features of the blood filter according to the invention. All embodiments closely correspond apart from the receiving compartment 2 being established in the blood filter only as shown in, e.g., FIGS. 1, 3, 5, 7, 9, and 10 and being established in part 2″ in the blood filter and in part 2′ in the syringe in, e.g., FIGS. 2, 4, 6, and 8.

In general, the blood filter according to the present invention comprises a receiving compartment 2; 2″ and a sampling compartment 10 separated by a filter membrane 6 and defined by a housing, preferably a housing comprising two parts one of which defines, preferably together with the filter membrane 6, the receiving compartment 2; 2″ the other one of which defined, preferably together with the filter membrane 6, the sampling compartment 10. Preferably, the parts of the housing are connected with one another at a sealed connector area, preferably defined be means of a snap fit or thread connection. Preferably, said connector area is also adapted to sealingly hold or engage the filter membrane for separating the receiving and sampling compartment.

According to a preferred additional and alternative embodiment (not shown), the blood filter and preferably the syringe comprises indicators suitable for conveying information to the user about the amount of blood to be inserted into the syringe and/or the blood filter as well as about the amount or way of travel the plunger of the syringe is to be pushed down to suitably insert the required volume of blood into the blood filter and to suitably build up the required pressure. Alternatively and/or additionally such indicators can include or can be replaced by means which limit the way of travel of the plunger accordingly in one and/or two directions to safeguard proper application of the method and use of the device/kit.

The blood filter according to the invention as depicted in FIG. 3 comprises a filter membrane 6 having opposite first and second sides, a receiving compartment 2 defining a hollow space and a sampling compartment 10 arranged on the second side of the filter membrane. The blood filter further comprises a hydrophilic and porous sheet 8 arranged on the first side of the filter membrane 6. In this regard, it is preferred that at least a part of the sheet is in direct contact with the filter membrane 6. This arrangement enables for the rapid and even distribution of the blood to be filtered throughout the filter membrane through capillary force.

FIG. 4 depicts a blood filter according to the invention comprising a filter membrane 6 having opposite first and second sides, a receiving compartment 2 defining a hollow space, wherein said receiving compartment comprises a syringe, and a sampling compartment 10 arranged on the second side of the filter membrane. The blood filter further comprises a hydrophilic an porous sheet 8 arranged on the first side of the filter membrane as described for FIG. 3.

The blood filter according to the invention as depicted in FIG. 5 comprises a filter membrane 6 having opposite first and second sides, a receiving compartment 2 defining a hollow space and a sampling compartment 10 arranged on the second side of the filter membrane. In this preferred embodiment of the invention, at least 50%, preferably at least 75%, more preferably at least 90% and most preferably at least 95% or the surface area of the second side of the filter membrane 6, i.e., the side which points to the sampling compartment, is in contact with a substantially flat substrate which is part of the sampling compartment 10. The sampling compartment according to this embodiment only comprises a small hollow space which may be formed either by thin channels arranged on said substantially flat substrate and/or solely by the space near the outlet 12 which is not in contact with said substrate.

In this preferred embodiment, the above described contact between the filter membrane 6 and the substrate which is part of the sampling compartment 10, preferably forms at least a part of the boundary of the sampling compartment promotes the accumulation of serum or plasma in the vicinity of the outlet 12.

An embodiment similar to that depicted in FIG. 5, i.e., with the special feature of the filter membrane 6 being in contact with said substrate is also depicted in FIG. 6. In this embodiment, a syringe is comprised in the receiving compartment 2 as described, e.g., for FIG. 2.

The preferred embodiment depicted in FIG. 7 is a combination of the embodiments of FIGS. 3 and 5. This means that the blood filter according to the invention as depicted in FIG. 1 further comprises a hydrophilic and porous sheet 8 arranged on the first side of the filter membrane as described for FIG. 3. Furthermore, in this preferred embodiment of the invention, at least 50%, preferably at least 75%, more preferably at least 90% and most preferably at least 95% or the surface area of the second side of the filter membrane 6, i.e., the side which points to the sampling compartment 10, is in contact with a substantially flat substrate which is part of the sampling compartment as described for FIG. 5.

In FIG. 8, the embodiments described for FIGS. 4 and 6 are combined. This means that the blood filter according to the invention as depicted in FIG. 2 further comprises a hydrophilic and porous sheet 8 arranged on the first side of the filter membrane as described for FIG. 4. Furthermore, in this preferred embodiment of the invention, at least 50%, preferably at least 75%, more preferably at least 90% and most preferably at least 95% or the surface area of the second side of the filter membrane 6, i.e., the side which points to the sampling compartment, is in contact with a substantially flat substrate which is part of the sampling compartment 10 as described for FIG. 6.

The blood filter depicted in FIG. 9 comprises the features as depicted and described in FIG. 1. The blood filter further comprises a nozzle 5 which reaches into the hollow space of the receiving compartment 2 and points towards the filter membrane 6. The nozzle can be of variable length, e.g., depending on the height of the receiving compartment 2 and/or on the volume of blood 1 to be filtered. In this embodiment, the blood can be directly applied to the filter membrane 6 through the nozzle without the danger of sticking to the side walls of the receiving compartment. This is especially suitable for small volumes of blood. The blood filter of this embodiment preferably further comprises a hydrophilic and porous sheet 8 arranged on the first side of the filter membrane as described for FIG. 3. It is even more preferred that, alternatively or in addition, at least 50%, preferably at least 75%, more preferably at least 90% and most preferably at least 95% or the surface area of the second side of the filter membrane 6, i.e., the side which points to the sampling compartment 10, is in contact with a substantially flat substrate which is part of the sampling compartment as described for FIG. 5.

The preferred embodiment as depicted in FIG. 10 is based on the blood filter of FIG. 9. The blood filter further comprises a disc 7 attached at the lower end of the nozzle 5 leaving an outlet for the blood lead through the nozzle. Said disc is constructed such that it does not completely span the blood filter in horizontal direction but leaves a gap 9 between the side boundary of the receiving compartment 2 and the disc. The principle underlying this embodiment of the blood filter of the invention is that blood lead through the nozzle towards the filter membrane 6 is guided to be evenly distributed on the filter membrane. The necessary pressure for filtration can still be created since the space underneath the disc is in communication with that above through the gap. The blood filter of this embodiment preferably further comprises a hydrophilic and porous sheet 8 arranged on the first side of the filter membrane as described for FIG. 3. It is even more preferred that, alternatively or in addition, at least 50%, preferably at least 75%, more preferably at least 90% and most preferably at least 95% or the surface area of the second side of the filter membrane 6, i.e., the side which points to the sampling compartment, is in contact with a substantially flat substrate which is part of the sampling compartment as described for FIG. 5.

FIG. 12A shows a preferred syringe to be used in combination with the inventive method and/or kit. In the situation shown in FIG. 12A, a predetermined second volume of blood 1 has already been inserted into the syringe. By pulling the plunger in the direction indicated by the arrow, a gas such as air fills a third volume 2'. This process can be continued until the plunger reaches a first stop 13, which is designed to prevent the plunger of being pulled out of the syringe (see FIG. 12B). The next step is to press the plunger downwards from the position shown in FIG. 12B in order to compress the third volume 2' until a predetermined pressure increase is achieved. In order to limit the compression of the third volume 2' a second stop 14 is provided, which is designed to stop the movement of the plunger during pushing downwards (see FIG. 12C). As shown in the sequence of FIGS. 12A-C, the second stop 14 will come into effect only after pulling the plunger all the way up towards the first stop. Thus, a user will be easily guided through the method steps according to the present invention: The user pulls a certain amount of blood into the syringe, then fills the remaining volume of the syringe with a gas such as air until the plunger is stopped by the first stop. Subsequently, the user simply has to push the plunger downwards until the movement of the plunger is again stopped, this time by the second stop. Preferably, as depicted, stop 1 is realized by means of a mechanical or fixed stopping shoulder and/or stop 2 is realized as a biased or snapfit member.

The blood filter according to the present invention is of particular advantage—in addition to the advantages already discussed in the preceding description—in that it allows the provision of a simple, easy to manufacture blood filter and a corresponding kit and method for filtering blood which can suitably be used also by untrained staff in a fast, easy and reliably way. The invention allows a ready to use provision of a blood filter and corresponding conductance of the method independent on place and time. Also very low amounts (volume) of blood can be filtered in a reliably and reproducible manner. This is of particular advantage when sampling blood of new born babies. The device can be easily stored such that it is kept clean and sterile and thus ready to use. Further advantages of the present invention will become apparent form the further specification.

What is claimed:

1. A method for filtering blood to produce plasma or serum, comprising the steps of:
   (a) providing a blood filter comprising
      (i) filter membrane having opposite first and second sides, wherein the filter membrane rests on a convex seating,
      (ii) a receiving compartment defining a hollow space for receiving a blood sample to be filtered and having a first volume, wherein said first side of said filter membrane is facing the receiving compartment, and
      (iii) a sampling compartment being arranged on said second side of said filter membrane, wherein at least 50% of the surface area of the second side of said filter membrane is covered by the convex seating being part of the sampling compartment;
   (b) inserting a blood sample and a gas into a syringe having a plunger, the blood sample occupying a second volume and the gas occupying a third volume in the syringe;
   (c) connecting said syringe to said blood filter to be in fluid communication with each other; and
   (d) increasing the pressure within said syringe by moving the plunger to a position such that the third volume is compressed by between 1/20 to 1/5, so that said blood sample is filtered by said filter membrane, wherein said plasma or serum comprised in said blood sample is forced through said filter membrane.

2. The method of claim 1, wherein said receiving compartment is made from a material that is adapted to withstand an internal pressure of at least 7 kPa without substantial deformation.

3. The method of claim 1, wherein at least 75% of the second side of said filter membrane is covered.

4. The method of claim 1, wherein the filter further comprises a hydrophilic and porous sheet arranged on the first side of said filter membrane in said receiving compartment.

5. The method of claim 1, wherein the convex seating comprises a plurality of channels for collecting the filtered blood sample.

6. The method of claim 5, wherein the plurality of channels cover between 0.5% and 15% of the surface of the convex seating.

7. The method of claim 6, wherein the plurality of channels forms a sampling compartment having a volume in the range between 0.06 mm$^3$ and 3.5 mm$^3$ per cm$^2$ of the filter surface.

8. The method of claim 1, wherein said receiving compartment is made from a material that is adapted to withstand an internal pressure of at least 18 kPa without substantial deformation.

9. The method of claim 1, wherein at least 90% of the surface area of the second side of said filter membrane is covered.

10. The method of claim 4, wherein the hydrophilic and porous sheet covers said filter membrane.

11. The method of claim 4, wherein the hydrophilic and porous sheet is made of fibrous material.

* * * * *